(12) United States Patent
Lubitz

(10) Patent No.: US 9,790,260 B2
(45) Date of Patent: Oct. 17, 2017

(54) VACCINE FOR TUMOR IMMUNOTHERAPY

(71) Applicant: Werner Lubitz, Klosterneuburg/Kritzendorf (AU)

(72) Inventor: Werner Lubitz, Klosterneuburg/Kritzendorf (AU)

(73) Assignee: Werner Lubitz, Klosterneuburg/Kritzendorf (AT)

( * ) Notice: Subject to any disclaimer, the term of this patent is extended or adjusted under 35 U.S.C. 154(b) by 0 days.

(21) Appl. No.: 13/665,145

(22) Filed: Oct. 31, 2012

(65) Prior Publication Data

US 2013/0115245 A1    May 9, 2013

Related U.S. Application Data

(60) Provisional application No. 61/557,532, filed on Nov. 9, 2011.

(30) Foreign Application Priority Data

Nov. 9, 2011 (EP) .................................... 11188494

(51) Int. Cl.
| | | |
|---|---|---|
| *C12N 1/20* | (2006.01) | |
| *C07K 14/47* | (2006.01) | |
| *A61K 35/15* | (2015.01) | |
| *A61K 39/00* | (2006.01) | |
| *A61K 39/39* | (2006.01) | |
| *A61K 39/108* | (2006.01) | |

(52) U.S. Cl.
CPC ...... *C07K 14/4748* (2013.01); *A61K 39/0011* (2013.01); *A61K 39/0258* (2013.01); *C12N 1/20* (2013.01); *A61K 2039/5154* (2013.01); *A61K 2039/5158* (2013.01); *A61K 2039/521* (2013.01); *A61K 2039/55594* (2013.01)

(58) Field of Classification Search
None
See application file for complete search history.

(56) References Cited

U.S. PATENT DOCUMENTS

| | | | |
|---|---|---|---|
| 7,361,360 | B2 | 4/2008 | Kitabwalla et al. |
| 7,740,872 | B2 | 6/2010 | Kitabwalla et al. |
| 7,968,323 | B2 | 6/2011 | Lubitz |
| 8,435,531 | B2 | 5/2013 | Kitabwalla et al. |
| 2003/0003511 | A1 | 1/2003 | Lubitz et al. |
| 2008/0031900 | A1 | 2/2008 | Palucka et al. |
| 2010/0196411 | A1 | 8/2010 | Duke et al. |
| 2011/0172826 | A1* | 7/2011 | Amodei et al. ............... 700/266 |
| 2012/0040829 | A1 | 2/2012 | Lubitz et al. |

FOREIGN PATENT DOCUMENTS

| | | |
|---|---|---|
| AU | 747328 | 5/2002 |
| AU | 778166 | 11/2004 |
| EP | 0000272 | 1/1979 |
| EP | 1897557 | 3/2008 |
| JP | 2002538198 | 10/2002 |
| JP | 2003521494 | 7/2003 |
| JP | 2009528987 | 8/2009 |
| WO | 99/06567 | 2/1999 |
| WO | 0053163 | 9/2000 |
| WO | 02/20042 | 3/2002 |
| WO | 03/006630 | 1/2003 |
| WO | 2004/058157 | 7/2004 |
| WO | 2009/090093 | 7/2009 |
| WO | 2010121180 | 10/2010 |

OTHER PUBLICATIONS

Eko et al Vaccine, 1999, 17:1643-1649.*
PCT/EP2012/072040, International Search Report and Written Opinion, Feb. 6, 2013.
Ardon et al., "Adjuvant Dendritic Cell-Based Tumour Vaccination for Children with Malignant Brain Tumours", Pediatr Blood Cancer, 2010, 54:519-525.
Haslberger et al., "Activation, stimulation and uptake of bacterial ghosts in antigen presenting cells", Journal of Biotechnology, 2000, 83:57-60.
Kudela et al., "Bacterial ghosts (BGs)—Advanced antigen and drug delivery system", Vaccine, 2010, 28:5760-5767.
Langemann et al., "The bacterial ghost platform system", Bioengineered Bugs, 2010, 1:5, 326-336.
Lubitz et al., "Applications of Bacterial Ghosts in Biomedicine", Pharmaceutical Biotechnology, 2009, 159-170.
Remondo et al., "Human dendritic cell maturation and activation by a heat-killed recombinant yeast (*Saccharomyces cerevisiae*) vector encoding carcinoembryonic antigen", Vaccine, 2009, 27:987-994.
Riedmann et al., "Bacterial ghosts as adjuvant particles", Vaccines, 2007, 6(2):241-253.
Bodey, et al., "Failure of cancer vaccines: the significant limitations of this approach to immunotherapy", Anticancer Research, 2000, 20: 2665-2676.
De Gruijl, et al., "Cancer vaccine strategies get bigger and better", Nature Medicine, vol. 5, No. 10, 1999, pp. 1124-1125.
Fields, et al., "Murine dendritic cells pulsed with whole cell tumor lysates mediate potent antitumor immune responses in vitro and in vivo", Proc. Natl. Acad. Sci.USA, vol. 95, Aug. 1998, pp. 9482-9487.
Forni, et al., "Immunoprevention of cancer: is the time ripe?", Cancer Research, vol. 60, No. 10., May 15, 2000, pp. 2571-2575.
Nestle, et al., "Vaccination of melanoma patients with peptide-or tumor lysate-pulsed dendritic cells.", Nature Medicine, vol. 4, No. 3, Mar. 1, 1998, pp. 328-332.
Palucka, et al., "Boosting Vaccinations with Peptide-Pulsed CD34+ Progenitor-Derived Dendritic Cells Can Expand Long-Lived Melanoma Peptide-Specific CD8+ T Cells in Patients with Metastatic Melanoma", Journal of Immunotherapy, vol. 28, No. 2, Mar. 1, 2005, pp. 158-168.
Rosenblatt, et al., "Dendritic cell fusion vaccines for cancer immunotherapy", Expert Opin Biol Ther, V5: (5), May 2005, 703-15.
Skornick, et al., "Inhibition of growth metastases in mice by immunization with cholesterol hemisuccinate-enriched tumor cells", Cancer Letters, vol. 25, No. 2, Dec. 1, 1984, pp. 153-161.

(Continued)

*Primary Examiner* — Mark Halvorson

(74) *Attorney, Agent, or Firm* — Kilpatrick Townsend & Stockton LLP

(57) ABSTRACT

The present invention relates to a vaccine comprising dendritic cells and bacterial ghosts for tumor immunotherapy.

24 Claims, 13 Drawing Sheets

(56) References Cited

OTHER PUBLICATIONS

Thurner, et al., "Vaccination with MAGE-3AI peptide-pulsed mature monocyte-derived dendritic cells expands regression of some metastases in advanced stage IV melanoma", J Exp Med, vol. 190, No. 11, Dec. 6, 1999, pp. 1669-1678.
Sonnenborn, et al., "The non-pathogenic *Escherichia coli* strain Nissle 1917—features of a versatile probiotic", Microbial Ecology in Health and Disease, vol. 21, No. 3-4, 2009, pp. 122-158.
Japanese Application No. 2014-5540437, English translation of Office Action mailed Jan. 25, 2016.
Haslberger, et al., "Activation, stimulation and uptake of bacterial ghosts in antigen presenting cells", Journal of Biotechnology, 2000, 83:57-66.
Kraśko et al., "Bacterial ghosts as adjuvants in syngeneic tumour cell lysate-based anticancer vaccination in a murine lung carcinoma model", Oncology Reports. 2016.
Michalek et al., "Oncolysate-loaded *Escherichia coli* bacterial ghosts enhance the stimulatory capacity of human dendritic cells", Cancer Immunology, Immunotherapy (2017): 66:149-159.

* cited by examiner

Phenotypic Profile

Migratory Capacity

Cytokine Profile

Figure 3:
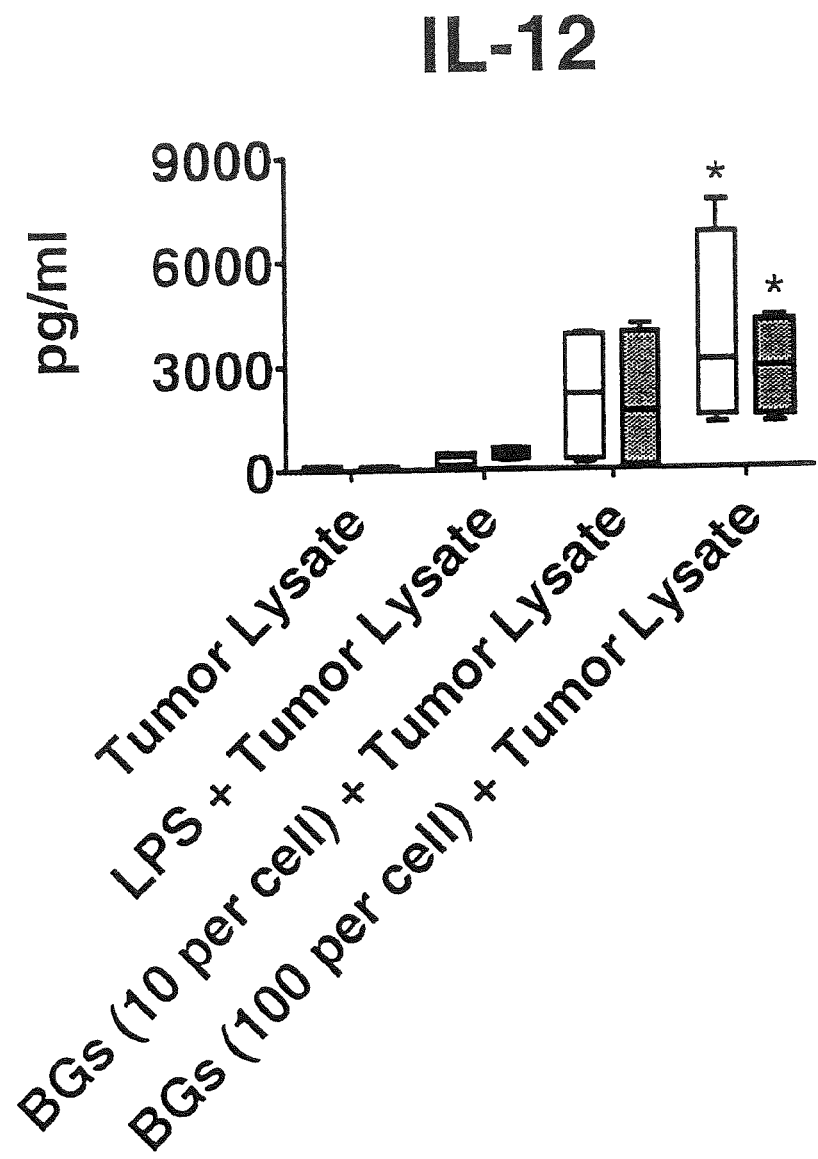

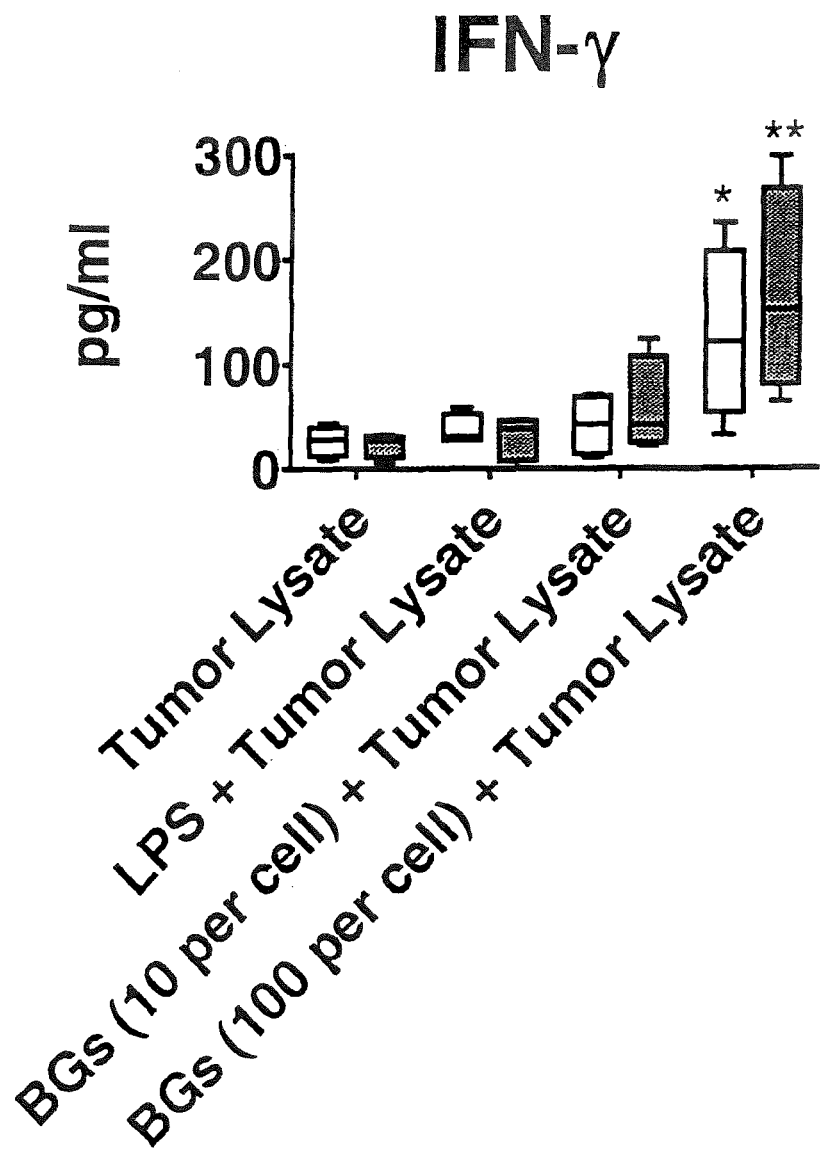
Figure 3 (continuation)
Cytokine Profile

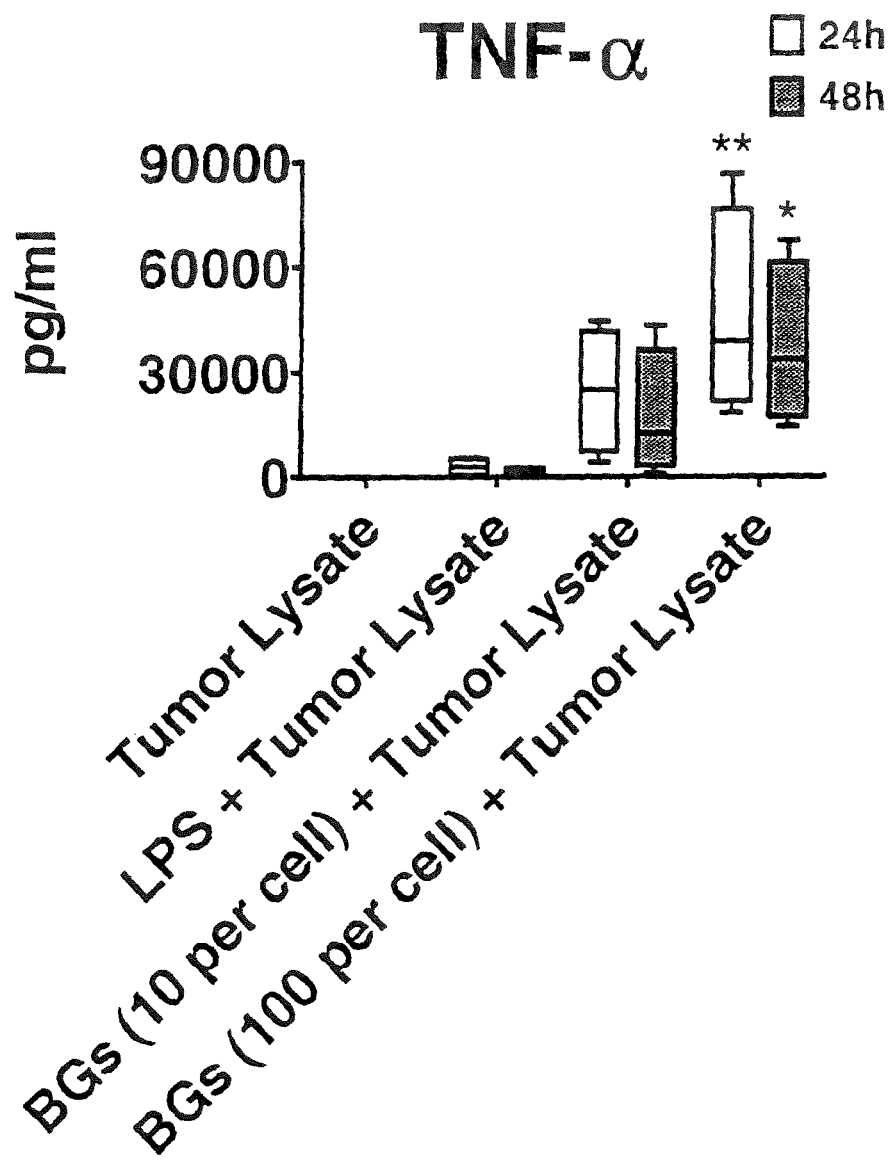
Figure 3 (continuation)
Cytokine Profile

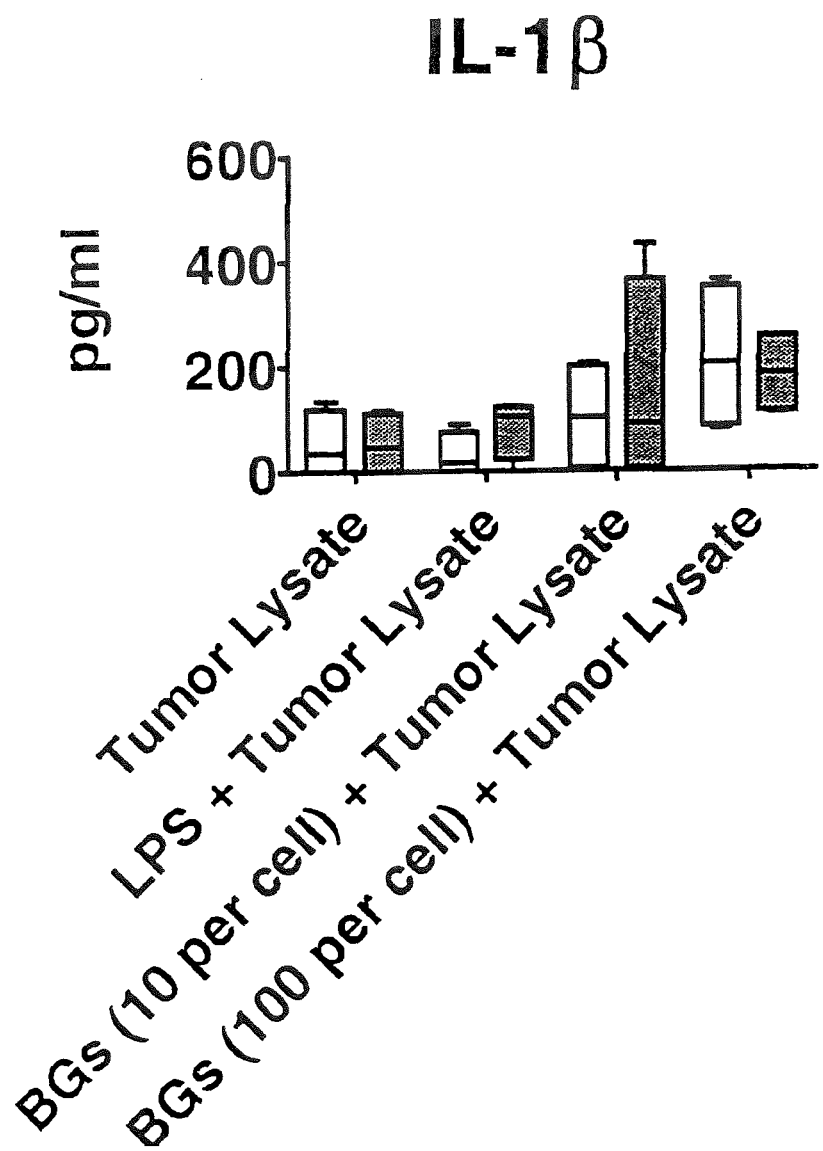
Figure 3 (continuation)
Cytokine Profile

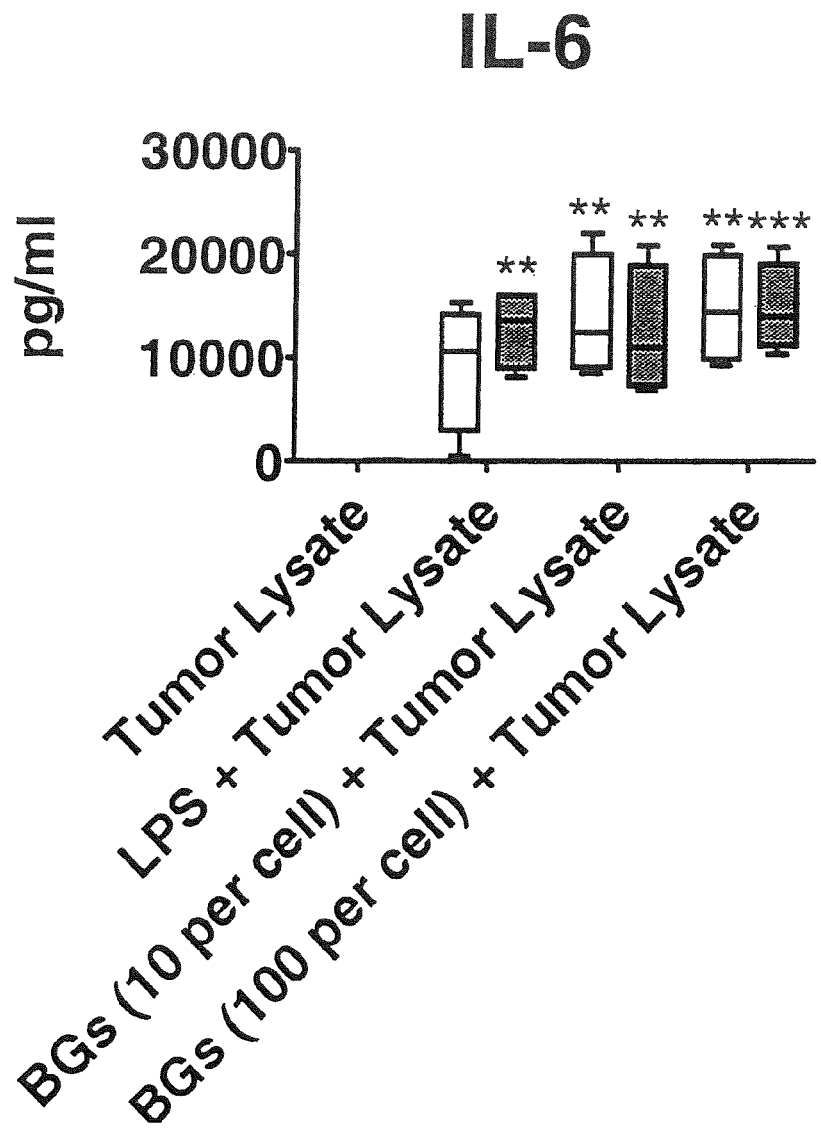
Figure 3 (continuation)
Cytokine Profile

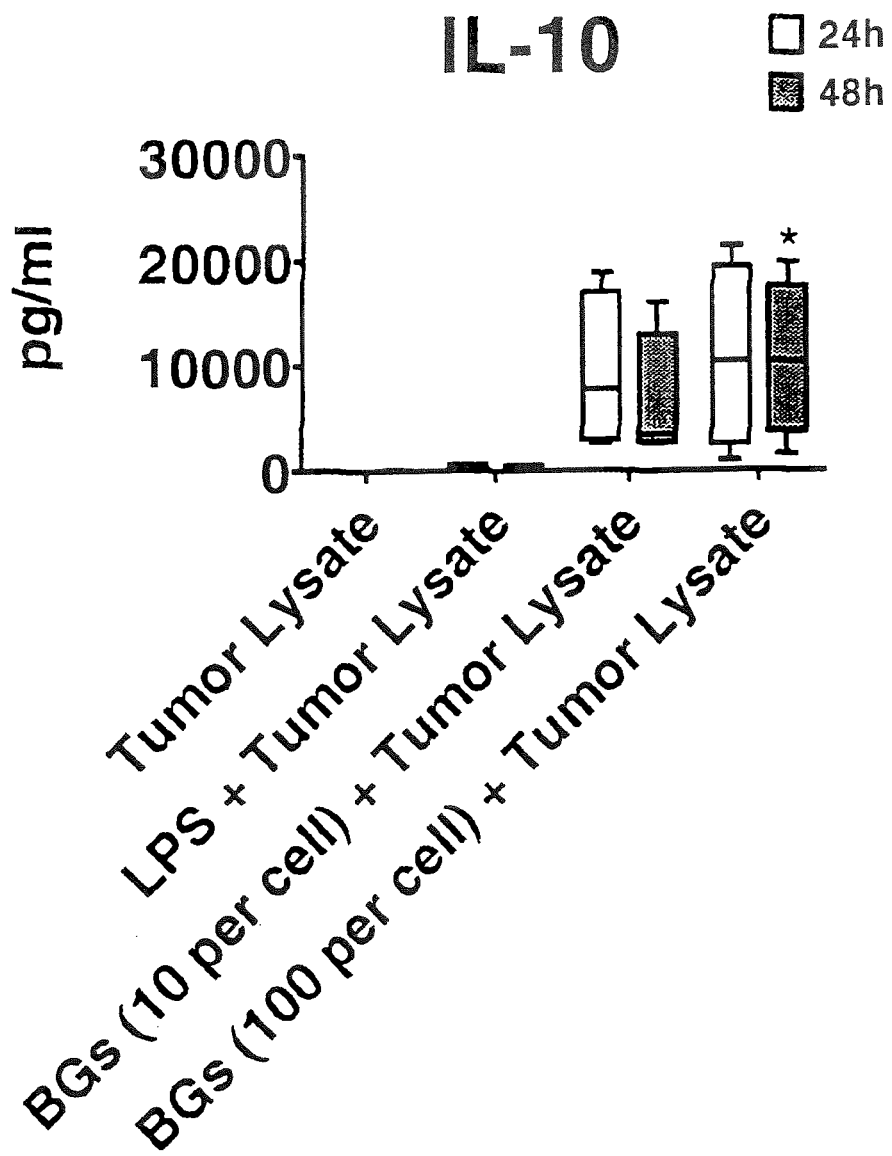
Figure 3 (continuation)
Cytokine Profile

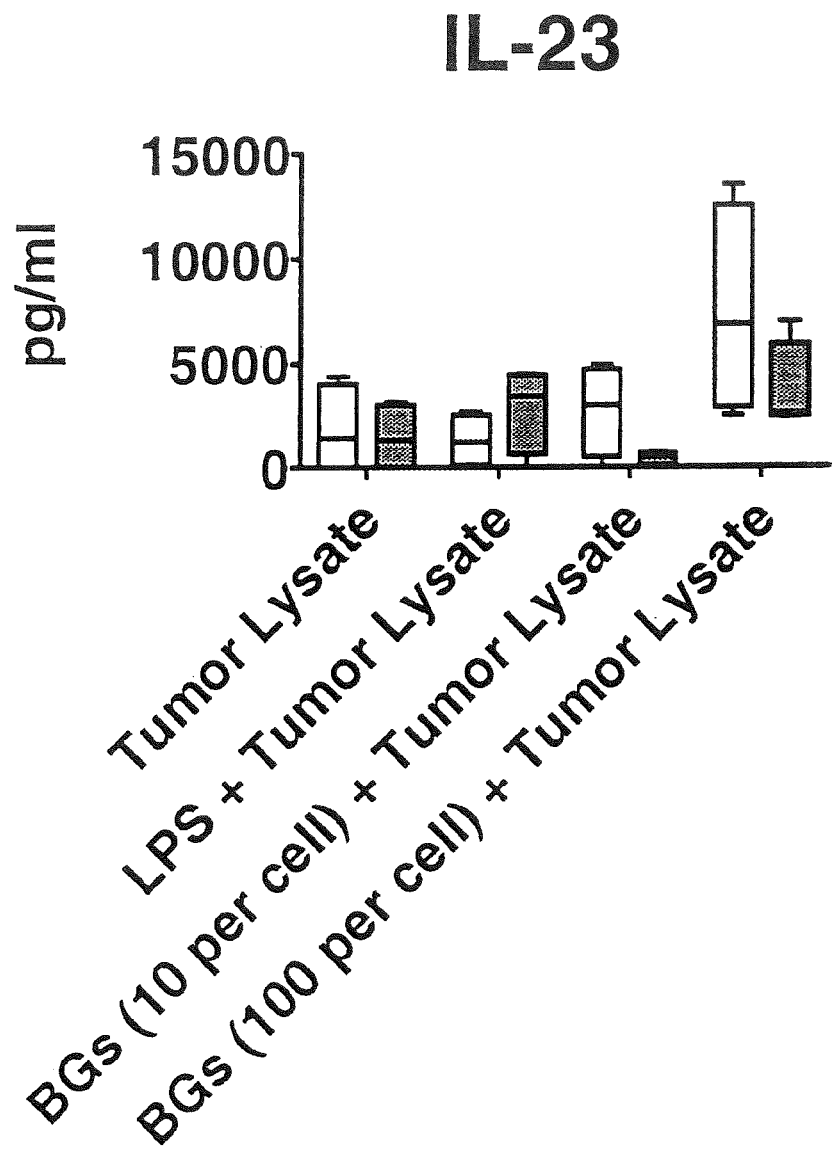
Figure 3 (continuation)
Cytokine Profile

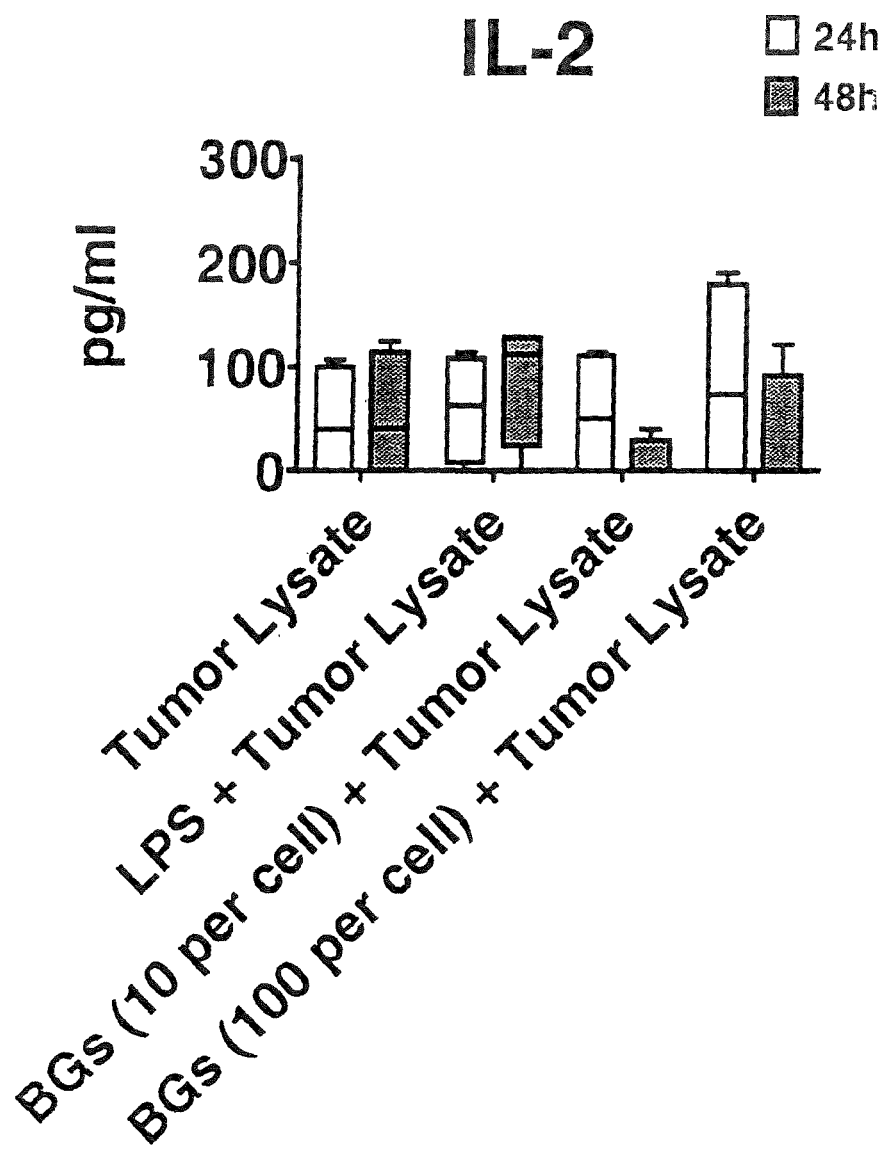
Figure 3 (continuation)
Cytokine Profile

Mixed Leukocyte Reaction

Tumor Recognition

Tumor Recognition

VACCINE FOR TUMOR IMMUNOTHERAPY

CROSS REFERENCE TO RELATED APPLICATIONS

This patent application claims priority to U.S. Provisional Patent Application No. 61/557,532, filed Nov. 9, 2011, and European Patent Application No. EP 11 188 494.6, filed Nov. 9, 2011.

DESCRIPTION

The present invention relates to a vaccine comprising dendritic cells and bacterial ghosts for tumor immunotherapy.

Dendritic cell-based therapy uses tumor cells to stimulate anti-tumor immunity. Thereby, dendritic cells are incubated with tumor cells, in particular, with autologous tumor cells (i.e. the patient's own tumor cells) to stimulate anti-tumor immunity. The dendritic cells incubated with tumor cells extract antigens directly from the tumor cells. The dendritic cells bearing the tumor-associated antigens are then used as vaccine to stimulate the immune system against the tumor. While dendritic cells are necessary to activate a response against cancer, they are often ineffective without prior activation because they fail to recognize growing cancers as dangerous. By activating dendritic cells, using an external stimulus, dendritic cells are created which present the relevant tumor-associated antigens and, thus, induce an effective anti-tumor response.

Such an approach is described, for example, in U.S. 2008/0031900. Therein, antigen-presenting cells such as dendritic cells are activated with GM-CSF and interferon alpha in the presence of one or more cancer cells.

While considerable progress has been made with such compositions, further improvement is still desired.

Therefore, the present invention provides a composition comprising
 (i) antigen-presenting cells (APCs),
 (ii) tumor-associated antigens (TAAs), and
 (iii) bacterial ghosts (BGs).

According to the invention, it has been found that the effectivity of antigen-presenting cells and, in particular, dendritic cells as tumor vaccine can be improved by providing a composition which additionally contains bacterial ghosts.

Bacterial ghosts (BGs) are empty bacterial cell envelopes of bacteria, in particular, of Gram-negative bacteria. Preferred bacteria are *E. coli* or *Shigella flexneri* 2a or *Mannheimia haemolytica* and, in particular, *E. coli* Nissle 1917.

BGs can be produced by controlled expression of heterologous gene causing disruption of bacterial membrane integrities and leading to lysis of the bacteria. An example of lytic gene is the bacteriophage PhiX174 gene E encoding a polypeptide triggering the fusion of the inner and outer membranes of the bacterial cells and forming trans-membrane tunnel structure spanning the whole cell envelope, through which the entire cytoplasmic content is expelled due to the change in osmotic pressures between the cell interior and the culture medium, whilst the inner and outer membrane structures are preserved and remain intact (cf. U.S. Pat. No. 7,968,323 B2). The size of the trans-membrane tunnel structure depends on the lysis conditions and inner diameter is in the range of 20-400 nm. The empty body of BGs is devoid of nucleic acids, ribosomes and other constituents, whereas essential inner and outer membrane structures including the antigenic molecules, e.g. outer membrane proteins, adhesins, lipopolysaccharide (LPS) and peptidoglycans are non-denatured and remain intact. There is absolutely no risk of reversal to pathogenic form after induction of controlled lysis process.

Bacterial ghosts may be prepared by a method comprising the following steps:
 (a) providing Gram-negative bacterial cells comprising a gene encoding a lytic protein capable of forming a tunnel structure in the bacterial cell envelope
 (b) optionally cultivating the bacterial cells under conditions wherein the lytic gene is not expressed
 (c) subjecting the bacterial cell to conditions wherein the lytic gene is expressed and the cytoplasmic components of the bacterial cells are liberated and
 (d) obtaining the resulting bacterial ghosts.

A preferred example of a gene encoding the lytic protein is the bacteriophage phiX174 gene E.

Particularly preferred, the bacterial cells used for the above described method of bacterial ghost preparation additionally encode an enzyme capable of hydrolyzing cytoplasmic components in the bacterial cell as described in WO 03/006630. The corresponding method of bacterial ghost preparation comprises the following additional steps:
 (a) optionally cultivating the bacterial cells under conditions wherein the enzyme gene is not expressed
 (b) subjecting the bacterial cell to conditions wherein the enzyme gene is expressed and the cytoplasmic components of the bacterial cells are degraded.

The gene encoding the hydrolytic enzyme is preferably a nuclease gene, in particular a *Staphylococcus aureus* nuclease gene (WO 03/006630).

BGs show no cytotoxic and genotoxic impacts on the viability and metabolic activity of a wide range of tested cells including macrophages, dendritic cells, tumor cells, endothelial cells and epithelial cells. BGs with their intact surface structures are efficiently recognized and phagocytosed by professional APCs, e.g. dendritic cells and macrophages through various surface receptors, e.g. complement receptors and Toll-like receptors. Moreover, further studies using dentritic cells (DCs) as model of the most professional antigen-presenting cells (professional APCs) revealed that their phagocytic activity and uptake of BGs depend on the bacterial strain used for the production of BGs.

Although the lysis process is very effective, there still might be a potential contamination with approximately one intact bacterial cell per 10,000 BGs. To avoid the presence of any living cell in a BG preparation, in particular, already before lyophilization of BG samples, an alkylating agent such as beta-propiolactone reacting and causing alterations in nucleic acids is preferably added to the fermentation system prior to final harvesting of BGs. A production process using beta-propiolactone for final inactivation meeting the criteria for application in human medicine and veterinary is disclosed in Patent Application No. PCT/EP2009/000272.

The use of bacterial ghosts as vaccine or adjuvant and the preparation of recombinant bacterial ghosts carrying heterologous proteins in their cell envelope structures are disclosed in Patent Application No. PCT/EP98/04723.

The use of bacterial ghosts as carrier or targeting vehicle of active compounds is disclosed in Patent Application No. PCT/EP00/01906.

The composition according to the invention comprises as component (i) antigen-presenting cells (APCs), in particular, professional antigen-presenting cells. In a preferred embodiment, the composition comprises monocytes and, most preferred, dendritic cells (DCs). In particular, the composition of the invention after incubation and ready for administration comprises mature tumor-associated antigen loaded DCs, preferably the tumor-associated antigen loaded DCs are tumor-associated antigen-presenting dendritic cells.

DCs are the most potent professional APCs as well as potent initiators and modulators of T cell responses in vivo including sensitization of MHC-restricted T cells, development of T cell-dependent antibody production, and induction of immunological tolerance. DCs have high phagocytic activity in both peripheral tissue and secondary lymphoid tissues, and capture antigens (Ag) via several mechanisms including macropinocytosis and receptor mediated endocytosis. The major role of DCs is related to the recognition of potential danger signals provided by foreign antigens, their internalization, processing and presentation within the complex of MHC class I and II molecules. In most cases during normal physiologic conditions, DCs are present in their immature state characterized by high phagocytic capacity, low expression of co-stimulatory and Ag-presentation molecules, and low cytokine production. Phagocytosis of soluble antigens by mannose receptors (uptake of glycosylated Ag) and Fc-receptors (uptake of immunoglobulins) strongly enhances efficiency of antigen presentation. Furthermore, DCs can present Ag in more than 100-fold lower concentrations after Ag complex with antibody is internalized through Fc-receptors compared to soluble Ag internalized via macropinocytosis. Effective T cell stimulation is strictly connected to DC maturation which affects cytokine production, expression of co-stimulatory molecules and presentation of peptide-MHC complexes. Endocytosis of extracellular antigens and their processing via endosomal-lysosomal pathway usually results in the presentation of antigen fragments within MHC class II molecules. However, endocytosis of extracellular antigens mediated through Fc-receptors allows MHC class I and class II restricted antigen presentation and induces DCs maturation. Presentation of extracellular antigens in the context of MHC class I molecules is known as cross-presentation or cross-priming. Efficient presentation of antigens by MHC molecules along with expression of co-stimulatory molecules and cytokine secretion leads to stimulation of various types of T cells, e.g Th1, Th2, Treg or Th17. For activation of Th1 lymphocytes and their proliferation sufficient production of IL-12 by mature DCs is important. Polarization toward Th1 type T cell immune response is considered as one of the most important factors necessary for induction of effective anti-tumor immune responses leading to recognition and elimination of tumor cells.

BGs show an excellent capacity to be recognized and internalized by professional APCs including DCs. DNA loaded BGs stimulate more efficiently both humoral and cellular Ag-specific immune responses than naked DNA in mice. An increase of IFN-gamma producing Ag-specific CD8+ T cells was observed in animals vaccinated with DNA loaded BGs in response to restimulation by APCs pulsed with peptide containing the immunodominant MHC class I epitope. Furthermore, BGs enhanced expression of MHC class I molecules and co-stimulatory molecules on DCs. Cross-presentation of tumor-associated Ag delivered to DCs by BGs could activate both CD4+ and CD8+ T cells and stimulates the immune system to enhance an immune response against tumor-associated Ag expressed by tumors.

Bacterial lipopolysaccharide (LPS) enhances maturation of DCs, affects endosomal acidification of DCs and also improves cross-presentation of Ag. Inner and outer membrane structures of BGs including LPS remain intact after protein E-mediated lysis of Gram-negative bacteria, therefore, besides high loading capacity, BGs also "carry" on the surface a LPS-highly effective molecule for stimulation of cross-presentation by DCs.

Thus, interaction between APCs and BGs in the inventive composition results in stimulation, activation and, thus, maturation of the APCs.

The composition according to the invention further comprises at least one tumor-associated antigen (component (iii)). Tumor-associated antigens (TAAs) can be provided e.g. by a tumor cell lysate. Preferably, an autologous tumor cell lysate is provided, i.e. a lysate from a tumor derived from the patient to be treated. However, it is also possible to use tumor-associated antigens from a tumor cell line.

Preferably, a tumor cell line of the same tumor type as the tumor to be treated is used. Preferably, at least two distinct tumor cell lysates are included in the composition according to the invention.

As a further alternative, the TAA may be carried by BGs. In one embodiment the BGs are loaded with TAA. In another embodiment the BGs carrying TAA are BGs carrying recombinant TAA (protein). Such BGs carrying recombinant TAA are derived from bacteria recombinantly expressing TAA.

Thus, the invention also relates to a composition wherein components (ii) and (iii) are coupled, e.g. in the form of BGs carrying recombinant TAA (protein). The tumor or cancer cells are preferably from cancers selected from the group consisting of fibrosarcoma, myxosarcoma, liposarcoma, chondrosarcoma, osteogenic sarcoma, chordoma, angiosarcoma, Kaposi's sarcoma, endotheliosarcoma, lymphangiosarcoma, lymphangioendotheliosarcoma, synovioma, mesothelioma, Ewing's tumor, leiomyosarcoma, rhabdomyosarcoma, rhabdosarcoma, colorectal carcinoma, colorectal adenocarcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, glioblastoma, astrocytoma, medulloblastoma, craniopharyngioma, ependymoma, pinealoma, hemangioblastoma, acoustic neuroma, oligodendroglioma, meningioma, neuroblastoma, retinoblastoma, myeloma, lymphoma, melanoma, and leukemia.

In an embodiment, the composition comprises a T98G tumor cell lysate.

More preferably, the composition comprises an autologous tumor cell lysate.

The composition of the invention may comprise tumor cells in a heat shocked, chemically treated or/and killed form.

The composition of the invention further optionally contains a cytokine, in particular, GM-CSF. Further, it optionally contains interferon alpha.

The invention, in particular, relates to an anti-tumor vaccine made of monocyte-derived dendritic cells (DCs), at least one, preferably at least two distinct tumor cell lysates from the same tumor type, bacterial ghosts (BGs) and, optionally, recombinant human granulocyte-macrophage colony-stimulating factor (GM-CSF), and interferon alpha (IFN-α).

The antigen-presenting cells in the composition according to the invention are activated and/or matured by incubation with tumor-associated antigens (TAAs) and bacterial ghosts (BGs). In particular, one or more antigen-presenting cells are activated that present one or more cancer antigens and induce T cell activation through incubation of the one or more antigen-presenting cells in the presence of one or more cancer cells, preferably in the presence of one or more tumor or cancer cell lysates, and in the presence of bacterial ghosts.

An advantage of the present application is that DCs can be incubated in the presence of tumor lysate obtained from autologous patient tumor cells and/or tumor cell lines prepared from identical histological tumor type. Thus, the DCs can be trained for the respective cancer type to be treated. Use of autologous tumor cells minimized the risk of infections or transfer of other diseases.

Another advantage is caused by incubation of DCs in the presence of tumor lysates made of two or more distinct cell lines obtained from identical tumor type. Thereby, the range of antigens presented by the DCs can be increased.

Intact surface immunostimulatory structures of BGs, optionally together with IFN-α and/or GM-CSF stimulate full maturation of DCs and elicit production of IL-12. GM-CSF is the cytokine typically used for generation of mature DCs.

Monocytes can be obtained from peripheral blood of patients by blood draw or leukapheresis, which guarantees a sufficient amount of cells.

Incubation with one or more tumor lysates provides for the presence of several tumoral tumor-associated antigens (TAA) and leads to the stimulation of broader TAA-specific immune responses.

Tumor lysates can be prepared either from autologous sample of tumor tissue obtained during patient's surgery or from tumor cell lines generated from the identical tumor type. Tissue donors are screened before surgery for sexually-transmitted diseases (STD), e.g. HIV, HCV, HBV, syphilis, and only negative patients are considered as tissue donors.

Anti-tumor vaccine based on DCs, tumor lysate and BGs can be applied as treatment for patients with tumors, in particular, with glioblastoma, renal carcinoma, ovarian carcinoma, prostate carcinoma, bladder carcinoma, colorectal carcinoma, colorectal adenocarcinoma, and melanoma. Preferably, tumor lysates are prepared from the respective tumor type and/or tumor cell lines.

The composition according to the invention preferably comprises empty bacterial ghosts as component (iii). However, it is also possible to use bacterial ghosts which are loaded, in particular, with an activator or silencer of the immune system. The bacterial ghosts can be loaded, in particular, with a pharmaceutical agent and/or DNA.

The composition may optionally contain bacterial lipopolysaccharide (LPS).

It was found that the APCs, in particular, dendritic cells contained in the inventive composition and being incubated with TAAs and BGs produce specific cytokines, in particular, IL-12, IL-23 and/or IL-1β.

When administering the matured APCs, in particular, DCs to a patient, an immune response is induced. It was found, in particular, that the inventive composition induces a Th17 response which was not observed when administering compositions of antigen-presenting cells which have not been incubated with bacterial ghosts.

The composition according to the invention preferably contains at least one bacterial ghost, more preferably at least five bacterial ghosts and more preferably at least 10 or at least 100 bacterial ghosts per antigen-presenting cell, in particular, per dendritic cell. The composition may contain up to 10,000 bacterial ghosts, preferably up to 1,000 bacterial ghosts and more preferably up to 500 bacterial ghosts per dendritic cell.

The invention further relates to a vaccine comprising the composition described herein. The composition may be combined with a pharmaceutically acceptable carrier or excipient before administration to the patent as a vaccine. Such pharmaceutically acceptable carriers or excipients are known to one of ordinary skill in the art. By administration of such a vaccine, an immune response against cancer cells is evoked. Thus, the invention also relates to a vaccine for tumor immunotherapy. When administered, the composition according to the invention and, in particular, the antigen-presenting cells comprised therein induce an increased tumor antigen recognition and, thus, tumor-specific killing by autologous T cells. Therefore the present invention also relates to a method of treating cancer in a patient comprising administration of the vaccine compositions described herein in an amount effective to treat cancer in the patient.

For administration, a vaccine preferably comprises from about 1 to 10 million cells, in particular, from 4 to 6 million cells per dose. Preferably, 5 to 15, in particular, 6 to 10 doses are administered. Administration can take place over several weeks. Preferably, the first two to three doses are administered weekly, followed by a monthly administration of the remaining doses.

For storage, the composition may be frozen or lyophilized. Preferably, the composition is frozen.

Administration can be performed in any suitable way, e.g. systemically, subcutaneously, intranodally, intradermally or intratumorally. Preferably the composition is administered subcutaneously, intranodally, intradermally or intratumorally.

For administration, bacterial ghosts may contain an active agent for activating or silencing the immune system. For maturating the APC, the bacterial ghost may contain additional ingredients such as tumor lysates, tumor peptides, tumor antigens or cytokines. Incubation of antigen-presenting cells with bacterial ghosts and tumor-associated antigen preferably takes place for a time range of from 10 min to 12 h, preferably from 15 min to 6 h, and more preferably from 3 h to 5 h.

In a particularly preferred embodiment, dendritic cells are cultured in commercially available CellGro® DC Medium GMP Serum-free Medium optimized for the generation of DCs, clinical ex vivo use, standardized, manufactured, tested and released in compliance with the relevant GMP-guidelines.

Preparation of anti-tumor vaccine according to the above-mentioned combination of stimulatory agents and DCs is preferably performed by incubation of monocytes, in particular, DCs obtained from peripheral blood of patients in a 5% $CO_2$ humidified incubator at +37° C. in CellGro® culture medium supplemented with DNAse for 2 h, followed by 3 days incubation in CellGro® culture medium supplemented with recombinant human GM-CSF and IFN-α in order to obtain a population of immature DCs. At least one tumor lysate, and preferably at least two tumor lysates, prepared from at least two distinct cell lines of identical tumor type are mixed together with BGs, vortexed and incubated for 1 h at room temperature (RT) with gentle shaking. Subsequently, recombinant human GM-CSF and IFN-α are mixed with the blend of BGs and tumor lysates, and added to immature DCs and incubated in a 5% $CO_2$ humidified incubator at +37° C.

After 10 min to 12 h of incubation, more preferably 4 h of incubation, non-internalized tumor lysates and BGs are carefully removed by gentle collection of media from DCs to a sterile 50 ml tube and spun down at 700 RPM/5 minutes/RT. Meanwhile, fresh CellGro® culture medium supplemented with recombinant human GM-CSF and IFN-α is added to the remaining cells. After centrifugation, the supernatant is quickly and carefully removed, the pellet is resuspended in CellGro® culture medium supplemented with recombinant human GM-CSF and IFN-α and the cells are returned back to the culture flask. DCs are incubated for additional 6 h in a 5% $CO_2$ humidified incubator at +37° C. before deep freezing of vaccine.

The invention is further described by the enclosed Figures and the following Examples.

Figure 1:
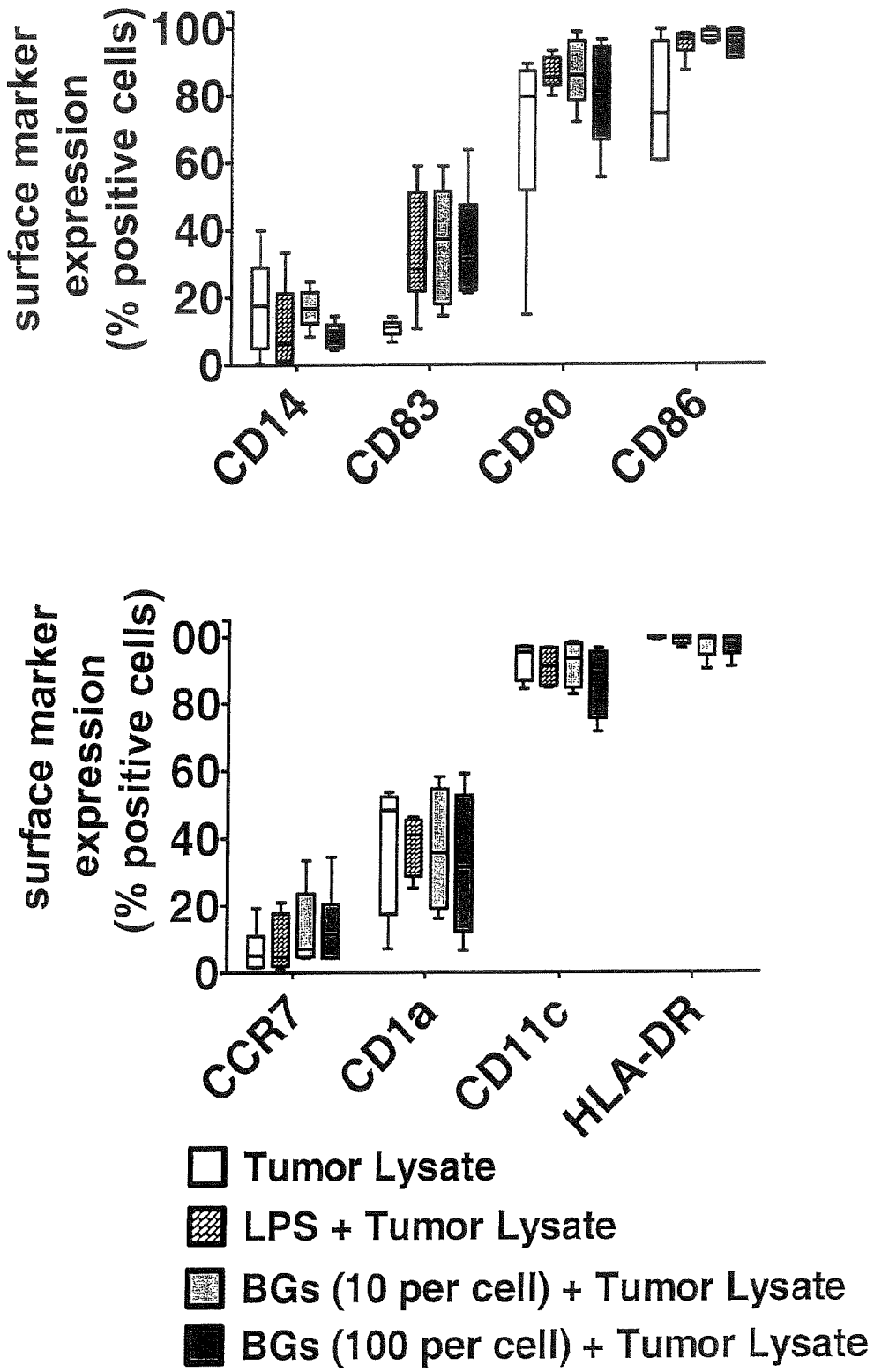

FIG. 1. The cell surface markers expression on DCs. Immature DCs were prepared by incubation of monocytes obtained from peripheral blood of normal healthy donors in CellGro® DC medium supplemented with IFN-α (3000 IU/mL) and rhGM-CSF (1000 IU/mL) for 3 days. Maturation markers of DCs were analyzed by multicolor flow cytometry 48 h after short (4 h) stimulation of immature DCs with tumor lysate and BGs from E. coli Nissle 1917 (10 and 100 BGs/1DC) in the presence of IFN-α and rhGM-CSF. Immature DCs incubated with IFN-α and rhGM-CSF and tumor lysate supplemented with Lipopolysaccharide (LPS) (200 ng/mL) or without extra maturation stimuli served as controls. The y-axis represents the percentage of cells expressing specific differentiation antigen. Data represent the mean±SD of 4 independent experiments performed using cells obtained from different donors.

CD14 is an indicator of maturation of dendritic cells. While monocytes show CD14 expression, matured dendritic cells show no or little CD14 expression. CCR7 is a marker for attractants of the cells to the lymph node. As can be seen from FIG. 1, expression of marker CCR7 increases for dendritic cells incubated with bacterial ghosts showing their mobility.

CD83 is a major marker of mature dendritic cells.

CD80, CD86, CD1a, CD11c and HLA-DR are maturation markers for dendritic cells.

Figure 2:
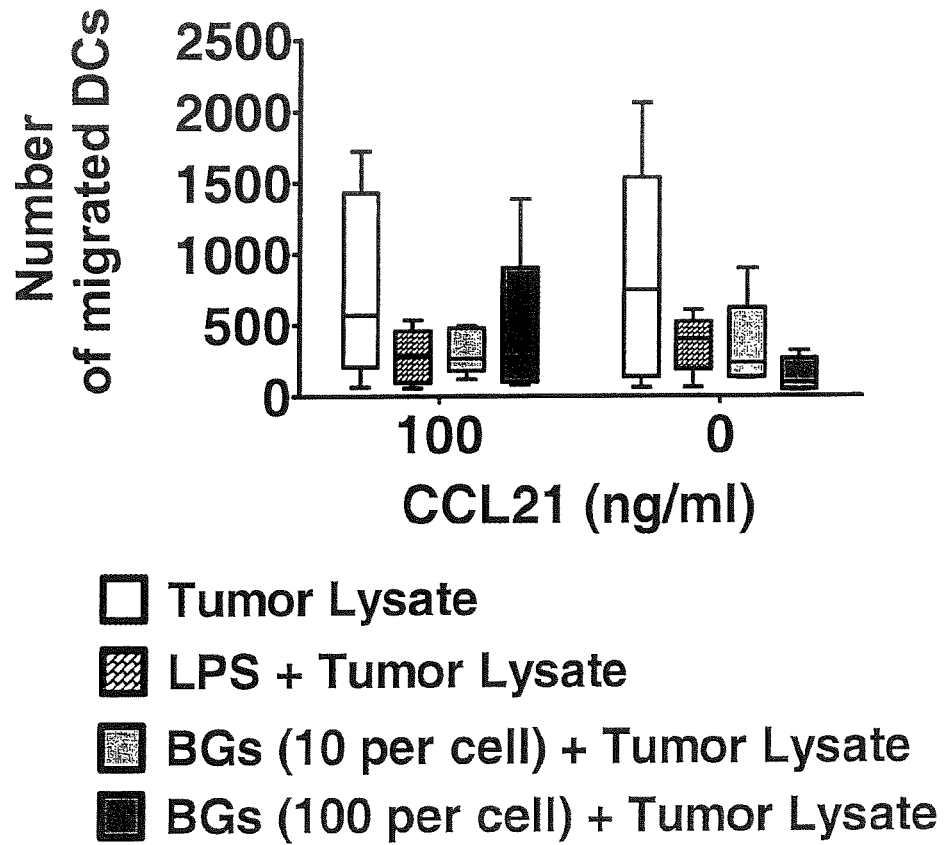

FIG. 2. Migratory capacity of DCs after incubation with tumor lysate and LPS or short stimulation with BGs. Chemotaxes of distinct DC populations matured in in the presence of IFN-α, rhGM-CSF and tumor lysate supplemented with BGs from E. coli Nissle 1917 (10 and 100 BGs/1DC), LPS (200 ng/mL) or without extra maturation stimuli in response to CCL21 (chemokine eliciting its effects by binding to a cell surface chemokine receptor CCR7) were determined as the number of cells which migrated into the lower part of a transwell system containing different concentrations of CCL21 and counted by flow cytometer. Each bar represents the mean number of migrated cells±SD of 4 independent experiments performed using cells obtained from different normal healthy donors.

FIG. 3. Cytokine profile of DCs matured in the presence of tumor lysate and LPS or short time incubation with BGs. Immature DCs were stimulated with IFN-α, rhGM-CSF and tumor lysate for short time (4 h) in the presence of pure LPS (200 ng/mL) or BGs from E. coli Nissle 1917 (10 and 100 BGs/1DC) prior to measuring cytokine released into supernatants after 24 h and 48 h incubations. Cells incubated without additional stimuli served as negative control. The levels of cytokines released from DCs were measured using FACSArray Bioanalyzer. Data represent the mean±SD of 4 independent experiments performed using cells obtained from various normal healthy donors. P values <0.05 were considered significant and are indicated with asterisks (*, P<0.05; , P<0.01; *, P<0.001).

IL-12 and IFN-γ are major activation markers for differentiation of T lymphocytes into Th1 type lymphocytes.

IL-23 (the growth and stabilization factor) and IL-6 (the differentiation factor) are cytokines involved in the development of Th17 lymphocytes. FIG. 3 shows that T helper cells are induced by compositions according to the invention.

IL-1β and TNF-α are pro-inflammatory markers.

IL-10 is an anti-inflammatory cytokine.

IL-2 is a T cell growth factor.

Figure 4:
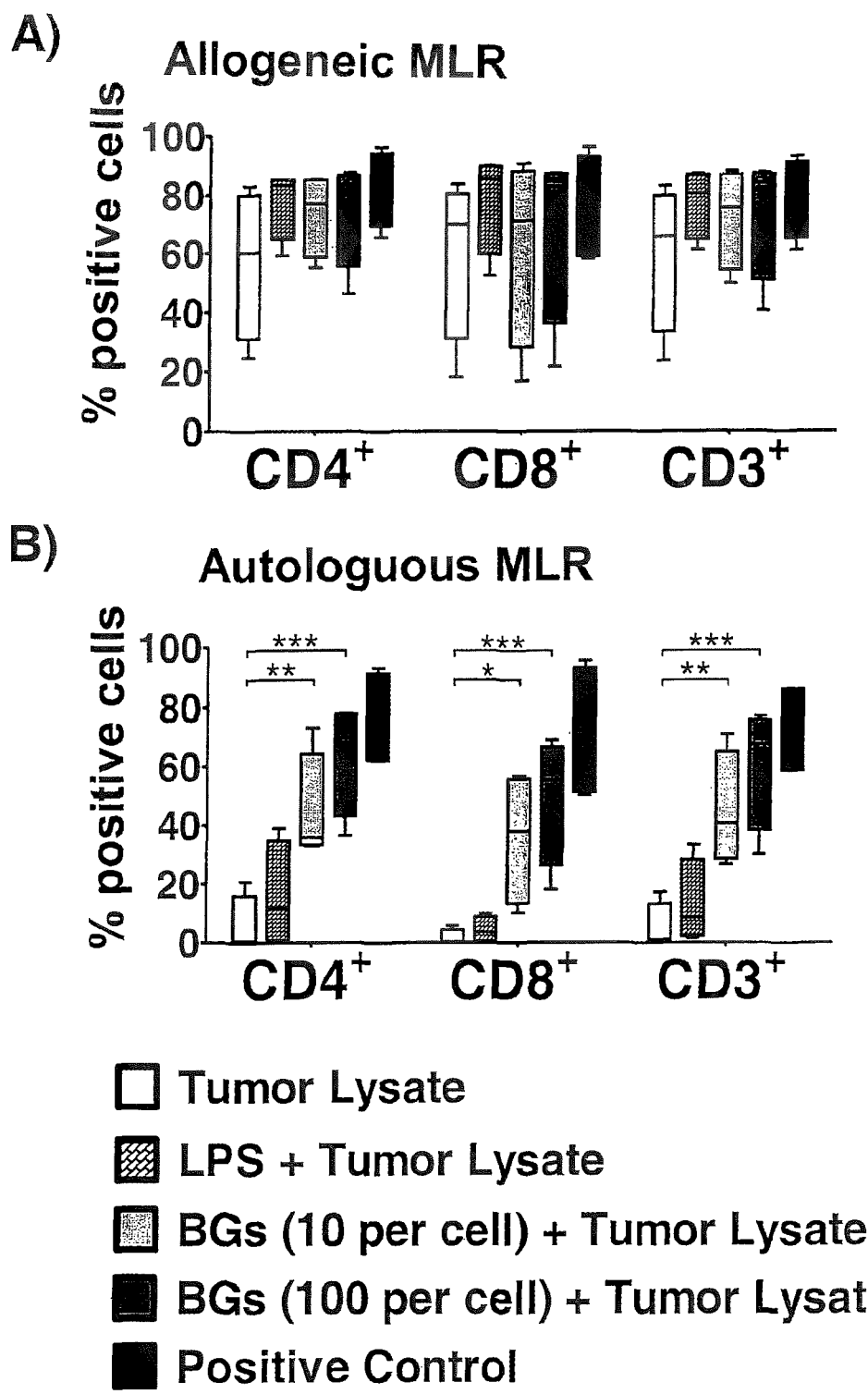

FIG. 4. Allogeneic (A) and autologous (B) immunostimulatory capacities of analysed DCs. Short time incubation of immature DCs with IFN-α, rhGM-CSF, tumor lysate and BGs (4 h) significantly enhanced capacity of DCs to stimulate proliferation of autologous T cells compared to DCs matured with IFN-α, rhGM-CSF and tumor lysate supplemented with pure LPS or without extra maturation stimuli. Autologous and allogeneic immunostimulatory capacities of analyzed DC populations were determined after 6 days of incubation in the presence of fluorescence-labeled (CFSE-labeled) allogenic or autologous T cells at the ratio DCs:T cells—1:10. Stimulated cells were stained after incubation with a panel of monoclonal antibodies (anti-CD3, anti-CD4, and anti-CD8) and proliferation of both autologous and allogeneic T cells was determined by multicolor flow cytometry. Values were calculated as percentage of T cells proliferated spontaneously subtracted from the percentage of cells proliferated after stimulation with distinct populations of DCs. T cells incubated with phytohemaglutinin (PHA) (5 µg/ml) served as positive control. Data represent the mean±SD of 4 independent experiments performed using cells obtained from different donors. P values <0.05 were considered significant and are indicated with asterisks (*, P<0.05; , P<0.01; *, P<0.001).

Figure 5A:
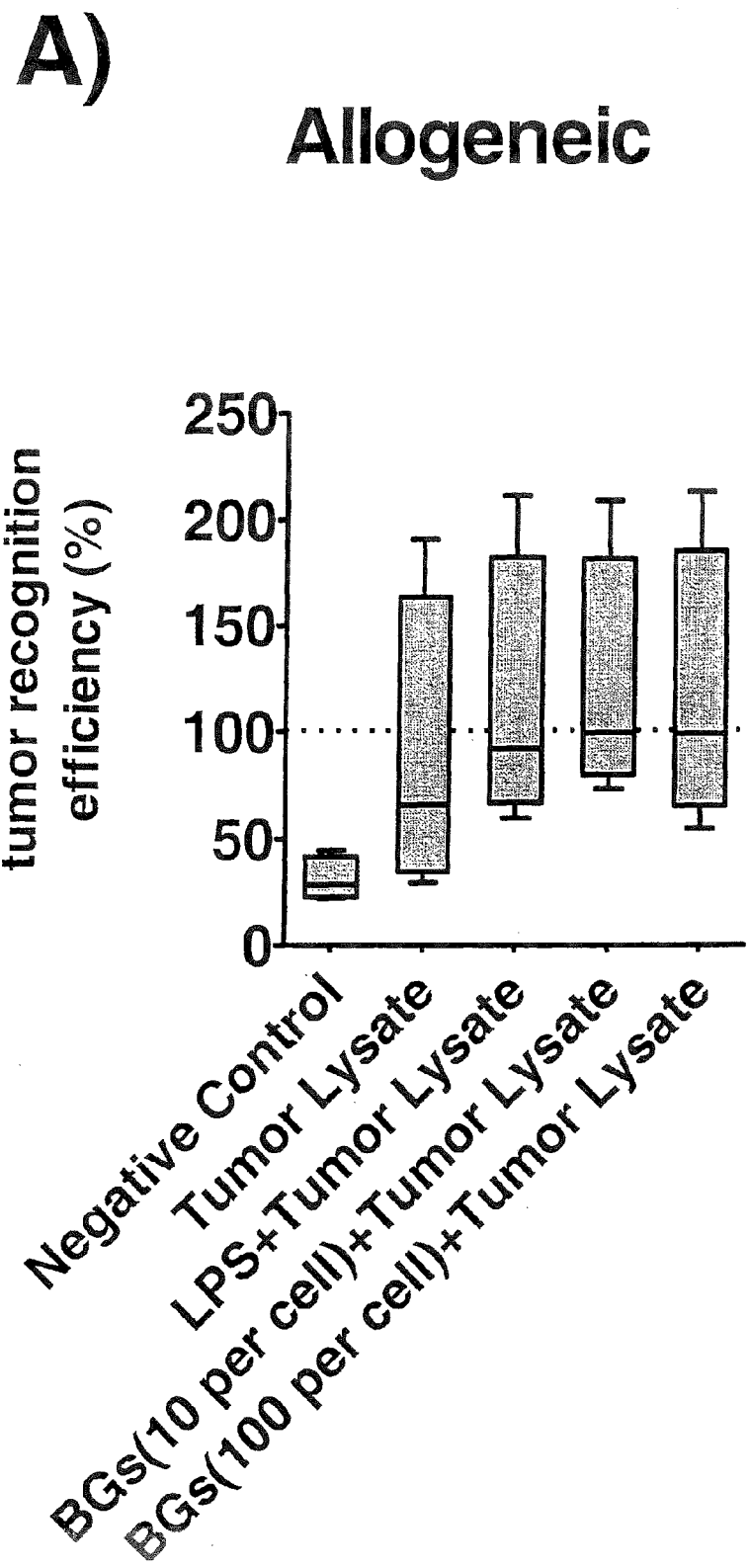
Figure 5B:
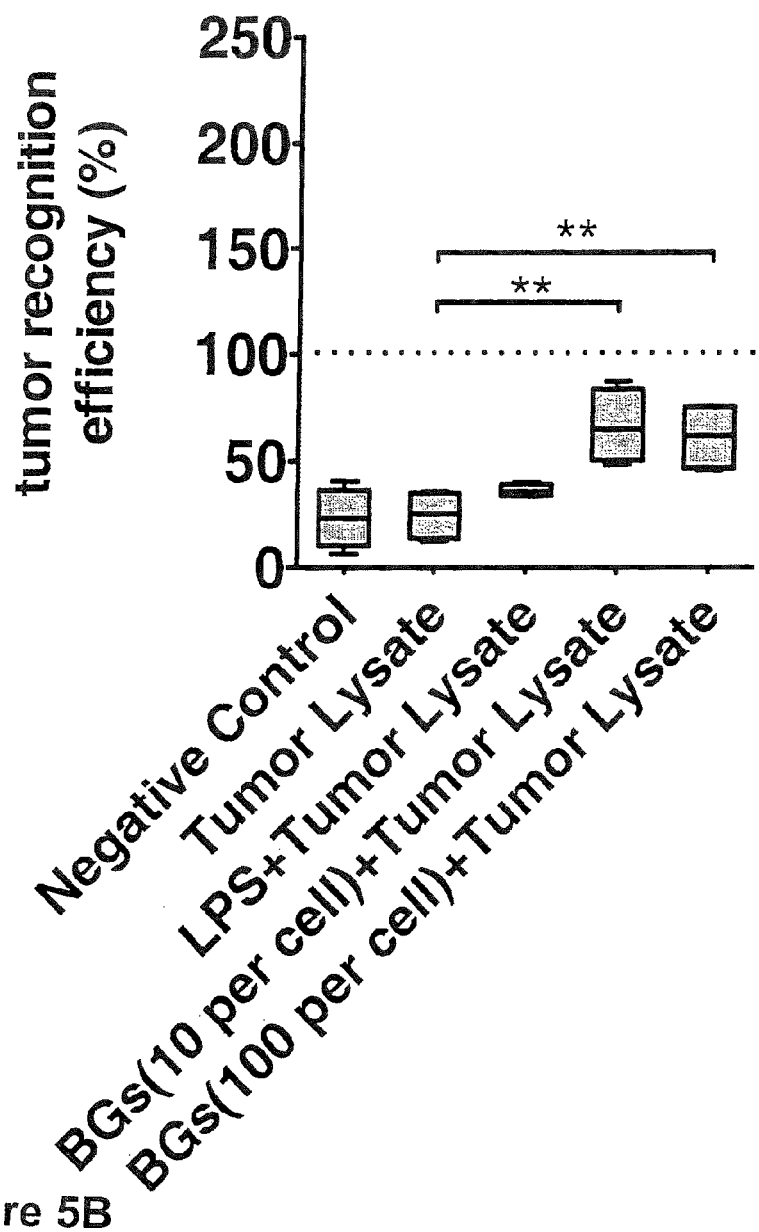

FIG. 5. Recognition of tumor cells and cytotoxic effects of allogenic (A) and autologous (B) T cells induced by DCs loaded with tumor lysate after short time stimulation with BGs. Allogeneic or autologous T cells were incubated for 6 days in the presence of tumor cell lysate (T98G cells) loaded DCs pre-stimulated with pure LPS (200 ng/mL), short time incubation (4 h) with BGs from E. coli Nissle 1917 (10 and 100 BGs/1DC) or without extra maturation stimuli. Subsequently, stimulated T cells were added to fresh fluorescence-labeled (CFSE-labeled) T98G tumor cells at the Effector:Target ratio 10:1. Specific lysis of tumor cells was determined 24 h after mutual co-incubation by flow cytometry. Lysis of tumor cells after incubation with 10% Et-OH served as positive control (100%). Tumor cells incubated without the presence of pre-stimulated effector cells served as negative control for spontaneous cell death. Data represent the mean±SD of 4 independent experiments performed using cells obtained from different donors. P values <0.05 were considered significant and are indicated with asterisks (*, P<0.05; , P<0.01; *, P<0.001).

In particular, the results of treatment of T98G tumor cells show a considerable enhancement for DCs+BGs compared to DCs alone or DCs+LPS.

In all experiments shown in FIGS. 1 to 5 human dendritic cells are included.

EXAMPLES

Example 1

Bacterial Ghosts

Bacterial ghosts are prepared in accordance with Patent Application No. PCT/EP2009/000272.

Example 2

Tumor Lysate Preparation

Tumor tissue obtained from a cancer patient or tissue culture plates (flasks) are stored in tubes filled with NaCl (0.9% sodium chloride in water for injection "Fresenius"). The tube with tumor tissue or cells are stored at +4° C. and processed up to 3 days after the surgery. The tube is irradiated (120 Gy) before processing of tissue. The donors (patients) have to be screened for sexually-transmitted diseases (STD), e.g. HIV, HCV, HBV, syphilis, and patients with positive detection of any of the mentioned diseases are excluded. Tumor tissue obtained from the patient is transferred to a sterile Petri dish filled with 5-10 ml HBSS (Hanks' Balanced Salt Solution; Lonza, No.: 10-547F or 10-527F; manufactured in accordance with cGMP regulations). Both necrotic and connective tissues are removed by scalpel and tweezers. Remaining tumor tissue is cut into small pieces of approximately 5 mm and ground by sterile syringe plunger. The obtained cell suspension is additionally homogenized by passing the suspension through a 20 G (0.9 mm) needle attached to a sterile syringe several times until a homogenized suspension is obtained. The cell suspension is subsequently filtered through a nylon strainer (100 μm) and collected in a sterile 50 ml tube. The Petri dish is washed with remaining HBSS, filtered through a nylon strainer and combined with filtered cells. The cell suspension is spun down at 1600 RPM for 7 min at +4° C. The supernatant is quickly and carefully decanted and a pellet is resuspended in 2 ml of CellGro® culture medium. Single cell suspension is equally divided into microtubes. The microtubes are placed into liquid $N_2$ or a mixture of dry ice and methanol for approximately 3 minutes. Subsequently, frozen cells are thawed at room temperature (RT) for 15-30 minutes until the cell pellet becomes completely melted (cells should not be kept at RT too long in order to prevent degradation of tumor cell proteins). The freezing-thawing procedure should be repeated 5 times. The cell lysate is then sonicated in an ultrasonic bath for 5 minutes. Cell debris together with cell lysate is collected in one tube, spun down at 10000-15000 RPM for 10 min, followed by quick and careful collection of the supernatant (cell lysates) using a fine needle separating off the pellet. Cell lysates should not be filtered and all steps have to be done under sterile conditions. Non-filtered cell lysates are aliquoted and stored at −80° C. until further use. The cell lysate is diluted with 10×DPBS (Dulbecco's Phosphate Buffered Saline, 10×PBS, Lonza, No.:17-515F). A spectrophotometer is used for determination of protein concentration.

Example 3

Culture of Monocyte-Derived Dendritic Cells for Anti-Tumor Vaccine Preparation Monocytes obtained from peripheral blood of patients are isolated either by elutriation (Elutra Cell Separation System, CaridianBCT Europe NV/SA) or magnetic separation (CliniMACS, Miltenyi Biotec GmbH). GM-CSF is dissolved in CellGro® culture medium to obtain a final concentration of $1 \times 10^5$ IU/ml and aliquoted into microtubes (700 μl per tube) and stored at −80° C. IFN-α (Roche, ROFERON-A $12 \times 10^6$ IU/ml) is aliquoted into microtubes (17.5 μl per tube) and stored between +2° C. and +8° C. Cryopreservation freeze media CryoStor CS2 or CryoStor CS5 are aliquoted under sterile conditions into microtubes (1.5 ml per tube). Separated monocytes are resuspended in culture medium and added into a culture flask, approximately $167 \times 10^6$ monocytes in 70 ml of culture medium. Approximately 150 μg of tumor lysate is required for one culture flask or tumor lysate from cells corresponding to a number of tumor cells 3 times that of immature DCs (monocytes). Monocyte cell suspension from culture flasks is centrifuged at 1500 RM for 10 min at RT. After decantation of supernatant the cell pellet is resuspended in a small volume of CellGro® culture medium and completed with CellGro® culture medium up to 35 ml. The cell suspension is transferred to a culture flask. GM-CSF (700 μl/$7 \times 10^4$ IU) and IFN-α (17.5 μl/$2.1 \times 10^6$ IU) in 35 ml of CellGro® culture medium are added to the monocyte cell suspension. The contents of the culture flask are carefully mixed by gently moving the flask from side to side. The cells are incubated in a 5% $CO_2$ humidified incubator at +37° C. for 3 days.

The prepared cell suspension of immature DCs is collected and distributed into 3 sterile 50 ml tubes. Fresh CellGro® culture medium (5 ml) is added meanwhile into each culture flask to avoid death of cells attached to the surface of culture flask. The cell suspension is spun down at 1500 RPM for 10 minutes at RT. Supernatant is quickly and carefully decanted and the cell pellets are resuspended in 2 ml of CellGro® culture medium and the cells from the culture flasks are transferred to 1 tube. Each of the tubes used for spinning of cells is gently rinsed with 4 ml of CellGro® culture medium and the content is transferred to the tube with collected cells. Tumor lysate (5 ml) obtained from tumor tissue or tumor cell lines (ratio of tumor cells:DCs=3:1; $501 \times 10^6$:$167 \times 10^6$) is mixed with $167 \times 10^8$ bacterial ghosts prepared from E. coli Nissle 1917 (ratio of BGs:DCs=100:1), vortexed thoroughly and incubated with gentle shaking at RT for 60 min. The mix of BGs and tumor cell lysate supplemented with GM-CSF (25 μl/$2.5 \times 10^4$ IU) and IFN-α (6.25 μl/$7.5 \times 10^4$ IU) is added to the DC suspension. Subsequently, the cell suspension with all reagents is transferred to a culture flask. The tube which contained the cell suspension is rinsed with 5 ml of CellGro® culture medium and the medium is transferred to the culture flask and carefully mixed with gentle shaking from side to side. The cells are incubated in a 5% $CO_2$ humidified incubator at +37° C. for 4 hours to allow internalization of BGs and tumor lysate and to start the maturation process. After 4 h of incubation, the cells are transferred to a 50 ml tube and the culture flask is gently rinsed with CellGro® culture medium. The medium used for rinsing of flasks is transferred to the tube with cell suspension. Fresh CellGro® culture medium (5 ml) is added meanwhile into the culture flask to avoid death of cells attached to the surface of the culture flask. The cell suspension is spun down at 1500 RPM for 10 minutes at RT. The supernatant is quickly and carefully decanted and cell pellets are resuspended in 20 ml of fresh CellGro® culture medium supplemented with GM-CSF (25 μl/$2.5 \times 10^4$ IU) and IFN-α (6.25 μl/$7.5 \times 10^4$ IU). The cell suspension is transferred into the original culture flask which is carefully and gently shaken from side to side, and the cells are incubated in a 5% $CO_2$ humidified incubator at +37° C. for additional 6 h.

Example 4

Storage of Anti-Tumor Vaccine Preparations

A culture flask with stimulated DCs obtained in Example 3 is thoroughly shaken to release cells adhered to the flask walls. The cell suspension is completely transferred to a labeled 50 ml tube. The culture flask is rinsed with two additional volumes of the same HBSS (10 ml) used for tumor lysate preparation, if possible, and the whole volume of HBSS is transferred to the tube with cell suspension. The original culture flask is filled with 5 ml of HBSS and placed back into an incubator. The volume of cell suspension is filled up to 50 ml with HBSS and gently mixed by tube overturns. The cell suspension is spun down at 1500 RPM for 10 minutes at +4° C. The supernatant is quickly and carefully decanted and cell pellets are resuspended first in 5 ml HBSS, followed by addition of additional 45 ml of HBSS and mixed well by tube overturns. 10 μl of cell suspension is used to determine the cell number, using a Bürkner counting chamber. If the concentration of cell within the suspension is below $1.4 \times 10^6$/ml, accutase should be used to release the remaining cells from culture flask, otherwise cell aliquots each containing of $5 \times 10^6$ cells will be frozen for future administration to the patient. It is mandatory to make at least 6 aliquots for administration to the patient, one aliquot for quality control, one aliquot for immunomonitoring, one aliquot for testing of mycoplasma and three aliquots for arbitrage. The cell suspension is spun down at 1500 RPM for 10 minutes at +4° C. Cryotubes are transferred to a pre-cooled MiniCooler. The supernatant is quickly and carefully decanted; cell pellets are resuspended in cryopreservation freeze media CryoStor CS2 and transferred to cryotubes. Immediately after aliquoting of anti-tumor vaccine preparation, all cryotubes are placed in an isopropanol box at −80° C. After 24 h in −80° C., all frozen vaccine preparation is transferred to a Dewar container filled with liquid nitrogen specifically set for anti-tumor vaccine preparation purposes use only.

TABLE 1

Standards for acceptability of anti-tumor vaccine preparations before administration to a patient.

| Test | | Criterion to pass quality control |
|---|---|---|
| Sterility of anti-tumor vaccine preparation | | STERILE |
| Detection of mycoplasma | | NEGATIVE |
| Cell count (×10$^6$) | | $1 \times 10^6 - 5 \times 10^6$ |
| Viability (%) | | 70-100% |
| DCs purity (%) | | 70-100% |
| Cell contamination | CD3 (%) | Total amount (CD3$^+$ + CD19$^+$) |
| | CD19 (%) | 0-30% |
| DCs phenotype* | CD80 (%) | 60-100% |
| | CD86 (%) | 60-100% |
| | MHC class II (%) | 60-100% |
| | CD83 (%) | 60-100% |
| | CD14 (%) | 0-40% |
| Production IL-12 (pg/ml) | | ≥100 pg/ml |
| Allogenic MLR-activated T-lymphocytes (%)** | DCs:PBMCs Ratio 1:5 | ≥30% |
| | DCs:PBMCs Ratio 1:10 | ≥30% |
| | DCs:PBMCs Ratio 1:20 | ≥15% |

*at least 3 of 5 phenotypic markers should meet the criteria to pass quality control before administration of anti-tumor vaccine preparation to a patient
**at least 2 of 3 examined ratios DCs:PBMCs in allogenic MLR tests should meet the criteria to pass quality control before administration of anti-tumor vaccine preparation to a patient

The invention claimed is:

1. A composition comprising:
   (i) antigen-presenting cells;
   (ii) at least one tumor cell lysate; and,
   (iii) bacterial ghosts from *E. coli* Nissle 1917.

2. The composition of claim 1 for use as vaccine for tumor immunotherapy.

3. The composition of claim 1, wherein the antigen-presenting cells comprise monocytes.

4. The composition of claim 1, wherein the antigen-presenting cells comprise dendritic cells.

5. The composition of claim 1, wherein the bacterial ghosts are obtained from bacterial cells comprising a gene encoding a lytic protein.

6. The composition of claim 1, wherein the bacterial ghosts have been treated with β-propiolactone.

7. The composition of claim 1, wherein the bacterial ghosts are loaded with an activator or silencer of the immune system, a pharmaceutical agent and/or DNA.

8. The composition of claim 1, wherein the bacterial ghosts carry recombinant tumor-associated antigens.

9. The composition of claim 8, wherein the bacterial ghosts are loaded with tumor-associated antigens.

10. The composition of claim 8, wherein the bacterial ghosts are derived from bacteria recombinantly expressing tumor-associated antigens.

11. The composition of claim 1, comprising from 1 to 10,000, or from 10 to 1,000 bacterial ghosts per antigen-presenting cell.

12. The composition of claim 1, comprising 1 to 10 million antigen-presenting cells per dose.

13. The composition of claim 1, wherein the antigen-presenting cells induce tumor-antigen recognition and tumor-specific killing by T cells.

14. The composition of claim 1, wherein antigen-presenting cells are autologous antigen-presenting cells.

15. The composition of claim 1, further comprising a pharmaceutically acceptable carrier or excipient.

16. A therapeutic vaccine comprising:
   (i) antigen-presenting cells;
   (ii) at least one tumor cell lysate;
   (iii) bacterial ghosts from *E. coli* Nissle 1917; and
   (iv) a pharmaceutically acceptable carrier or excipient.

17. A method of treating cancer in a patient comprising: administering to the patient a therapeutic vaccine composition comprising
   (i) antigen-presenting cells;
   (ii) at least one tumor cell lysate;
   (iii) bacterial ghosts from *E. coli* Nissle 1917; and
   (iv) a pharmaceutically acceptable carrier or excipient,
in an amount effective to treat the cancer in the patient.

18. The method of claim 17, wherein the therapeutic vaccine composition is prepared by a process comprising a step of incubating the antigen-presenting cells with the at least one tumor cell lysate in presence of the bacterial ghosts for 10 minutes to 12 hours.

19. The method of claim 18, wherein the antigen-presenting cells are dendritic cells.

20. The method of claim 19, wherein after the incubation the dendritic cells exhibit an increase in one or more of levels of cytokine release, expression of CD83, expression of HLA-DR, expression of CD80, expression of CD86 and capacity to stimulate proliferation of autologous CD4$^+$ and CD8$^+$ T-cells, in comparison with a composition prepared by a process comprising a step of incubating the dendritic cells with the at least one tumor cell lysate without the presence of the bacterial ghosts.

21. The composition of claim 1, wherein the composition is prepared by a process comprising a step of incubating the antigen-presenting cells with the at least one tumor cell lysate in presence of the bacterial ghosts for 10 minutes to 12 hours.

22. The composition of claim 1, wherein the antigen-presenting cells are dendritic cells.

23. The composition of claim 22, wherein the composition is prepared by a process comprising a step of incubating the dendritic cells with the at least one tumor cell lysate in presence of the bacterial ghosts for 10 minutes to 12 hours.

24. The composition of claim 23, wherein after the incubation the dendritic cells exhibit an increase in one or more of levels of cytokine release, expression of CD83, expression of HLA-DR, expression of CD80, expression of CD86 and capacity to stimulate proliferation of autologous $CD4^+$ and $CD8^+$ T-cells, in comparison with a composition prepared by a process comprising a step of incubating the dendritic cells with the at least one tumor cell lysate without the presence of the bacterial ghosts.

\* \* \* \* \*